United States Patent [19]

Carlsson et al.

[11] 4,232,119

[45] Nov. 4, 1980

[54] REAGENT FOR USE IN IMMUNOCHEMICAL ASSAY METHODS

[75] Inventors: Jan P. E. Carlsson, Uppsala; Rolf E. A. V. Axén, Bälinge; Håkan N.Y. Drevin, Brunna, all of Sweden

[73] Assignee: Pharmacia Diagnostics AB, Uppsala, Sweden

[21] Appl. No.: 882,545

[22] Filed: Mar. 2, 1978

[30] Foreign Application Priority Data

Mar. 4, 1977 [SE] Sweden ............................ 7702464

[51] Int. Cl.² .......................................... C12Q 1/66
[52] U.S. Cl. ........................................ 435/7; 424/1; 424/12; 260/112 R; 260/112 B; 23/230 B
[58] Field of Search .................. 195/63, 68, 103.5 A; 424/1, 12; 260/112 R, 112 B; 23/230 B; 435/7

[56] References Cited

U.S. PATENT DOCUMENTS

| | | | |
|---|---|---|---|
| 4,002,532 | 1/1977 | Weltman et al. | 424/12 X |
| 4,004,979 | 1/1977 | Avrameas et al. | 195/68 |
| 4,048,416 | 9/1977 | Axén et al. | 195/63 X |

*Primary Examiner*—Lionel M. Shapiro
*Attorney, Agent, or Firm*—Fred Philpitt

[57] ABSTRACT

A reagent for use in immunochemical assay methods carried out in the presence of an aqueous liquid, which reagent comprises a conjugate of one or more molecules of immunoglobulin and one or more units of an analytically indicatable group which molecules and units are bound together via bridges containing the group, —S—S—, said conjugate being soluble in said aqueous liquid.

5 Claims, No Drawings

REAGENT FOR USE IN IMMUNOCHEMICAL ASSAY METHODS

The present invention relates to a reagent for use with immunochemical assay methods carried out in the presence of an aqueous liquid.

A large number of immunochemical assay methods are known in which there is used as a reagent a water-soluble reagent comprising immunoglobulin labelled with at least one analytically indicatable group. See, for example, Radioimmunoassay Methods (Editors: K E Kirkham and W M Hunter, Churchill Livingstone, London 1971) for example pages 405-412 of the article "Solid Phase Antigen Antibody Systems" by L Wide.

In this connection said immunoglobulin is often an antibody directed against an antigen or hapten. Said immunoglobulin, however, may also function, as, for example, antigen or protein A reactive component in such assay methods. It is also well known that said immunoglobulin may belong to different immunoglobulin classes (e.g. the classes IgG, IgM or IgE). The term "immunoglobulin" includes in this context also modified immunoglobulin (e.g. aggregated) as well as fragments thereof (e.g. Fab- or Fc-fragments) which exhibit an affinity to another counterpart involved in the assay method. Preferably, however, said immunoglobulin is an antibody.

In immunochemical assay methods it is well known that said analytically indicatable group may, for example, be a radioactive, a fluorescent, a luminescent, a chromophoric or an enzymatically active group. The enzymatically active group may for example be an enzyme selected from the group hydrolases, oxidases and reductases but also other types of enzymes may be used.

For the purpose of labelling the immunoglobulin with an analytically indicatable group, it is possible to directly couple said immunoglobulin chemically with the labelling group or to introduce a bridge therebetween. This chemical reaction can be effected, for example, by making use of amino groups in one of the reactants and carboxyl groups in the other, or amino groups in both of the reactants. When coupling (conjugating) by means of a bridge, it is known, for example, to use such reactants as glutardialdehyde, cyanogen bromide and carbodiimides. Methods known hitherto for coupling the components together are, however, encumbered with a number of disadvantages.

Thus, the activity and specificity of the immunoglobulin-molecule can be changed as a result of the conjugation (as can also the activity and specificity of an enzyme when used for labelling). Subsidiary reactions leading to aggregates of solely the one type of molecule can occur. (It is particularly disadvantageous in this respect if these reactions lead to a complex containing only immunoglobulin). Further, subsidiary reactions often result in a large quantity of undesirable high molecular weight aggregates. Finally, the known methods result in a substantial amount of unreacted material. When using glutardialdehyde as the coupling agent, there is also formed polymers of glutardialdehyde itself of approximately the same size as the conjugate. These polymers may contain reactive structures which are able to react with the conjugate long after the surplus glutaraldehyde has been removed from the reaction mixture, and impair its immunochemical and (when enzymatically labelling) enzymatic activity. Consequently, the known methods result in a highly heterogeneous product mixture, whose working-up with respect to the desired conjugate involves much work and is relatively time-consuming. Furthermore, the yields are often very low.

In accordance with the invention there has now been provided an improved conjugating technique in which the aforementioned disadvantages have been eliminated to a substantial extent. This technique is based on thiol-disulphide-exchange. In accordance with one embodiment of this technique one or more thiol-groups (to the extent that they are not already present) are introduced into one of the two types of molecules to be included in the conjugate (either into the immunoglobulin or into the labelling substance such as an enzyme) and one or more disulphide structures activated for thiol disulphide exchange in the other type of molecule, i.e. if a thiol group is inserted into the labelling substance, the immunoglobulin molecule is provided with disulphide structure and vice versa. The two modified types of molecule are then brought into contact with each other, whereupon they are bound to each other by an —S—S—bond via the thiol disulphide exchange reaction.

In accordance with a further embodiment of said technique there is used an inert carrier substance (e.g. a water-soluble polymer as carrier) which is soluble in the liquid in whose presence the immunochemical reaction is carried out, disulphide structure activated for thiol disulphide exchange being introduced into the soluble carrier and one or more thiol groups in both the labelling substance and the immunoglobulin, whereafter the labelling substance and the immunoglobulin are bound to the carrier (for example a polymer) whilst establishing —S—S—bonds by thiol disulphide exchange reaction.

Accordingly, the reagent according to the invention is characterized by the fact that it comprises a conjugate of one or more molecules of immunoglobulin and one or more units of an analytically indicatable group, which molecules and units are bound together via bridges containing the group —S—S—, said conjugate being soluble in the aqueous liquid.

The analytically indicatable group, in accordance with the invention, is preferably an enzymatically active, radioactive, chromophoric, fluorescent or luminescent group.

Preferably there is found on both sides of the —S—S—bridge a carbon atom which may form part of an aliphatic or aromatic group. The said carbon atoms are, in turn, preferably bound to at least one carbon atom. Remaining bonds of the first mentioned carbon atoms are preferably saturated with hydrogen atoms. Each of the first mentioned carbon atoms may, for example, be included in the group —CH$_2$— and/or

where the carbon atom is seated in an aromatic ring, such as a benzene ring. Consequently, the disulphide bridge is preferably seated in a group of the formula

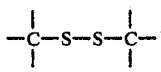

where one of the remaining bonds of each of said carbon atoms passes to another carbon atom and remaining bonds of each carbon atom pass to hydrogen and/or carbon.

According to another embodiment of the reagent according to the invention, the bridges contain a group of the formula

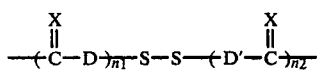

in whixh X are mutually the same and signifies O or NH, D and D' are mutually the same or different and signify the group $$-CH-CH_2-CH_2- \quad \text{or} \quad -(CH_2)_m-,$$
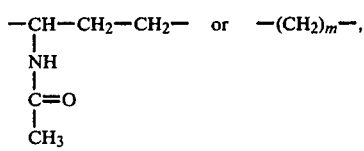

where m is an integer from 1-3, and $n_1$ and $n_2$ are the same or different and each signifying 0 or 1. For example, the group

and/or the group

may be the group

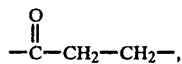

the disulphide bridge being bonded to the .CH$_2$-group.

According to another aspect of the invention, a preferred reagent is characterized in that the molecules of the immunoglobulin component and the units of the analytically indicatable group are each bound to a water-soluble carrier, wherewith at least one of said component and said group are bound to the carrier via bridges containing the group —S—S—.

The conjugating technique utilized in accordance with the invention also affords the particularly valuable advantage, as compared with previously known techniques, that the conjugate formed is reversibly splittable in a reducing environment, which can be utilized to increase the sensitivy of the assay methods when the conjugate is used. For example, enzymes, conjugated as analytically indicatable groups to some other macromolecule, often exhibit lower activity than corresponding native enzymes. This reduction in activity is due to the fact that the enzyme, as a result of the conjugation, is sterically prevented from acting on its substrate. A further reason may be the diffusion control which often occurs in the water layer nearest the enzyme conjugate. When a conjugate, held together by means of one or more bridges containing the group —S—S— in accordance with the invention, is used, the enzyme label may be split off by methods known in connection with the breaking up of —S—S—bridges, for example by reduction of thiol disulphide exchange, whereafter the enzyme activity can be measured in a liquid phase, whereby optimum enzyme activity is obtained. This also enables the use of water-insoluble substrates for enzyme assay. (This naturally assumes that there is selected conditions such that when splitting, the enzyme label used is not inactivated or that the measuring system used is not unfavourably influenced by the environment used to split the bridge). Even in those cases when the analytically indicatable group comprises, for example, a fluorescent or radioactive molecule, it is highly favourable that these molecules can be split off from the immunoglobulin, since they then can readily be measured without radiation absorbing effects caused by other conjugate participants and solid phase.

For the purpose of introducing a thiol group in one of the two types of molecules which shall be included in the conjugate, it is possible to use known thiolating agents such as thiolimidate of the formula

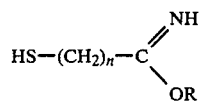

where R is methyl or ethyl and n is an integer from 1-10, preferably 2-4 or N-acetyl homocystein thiolactone.

The reaction is carried out in an aqueous solution, in a slightly alkaline environment (pH 7-9) and a temperature of 15°-30° C., with a large surplus of thiolating agent.

For the introduction of a disulphide structure activated for thiol disulphide exchange, there can also be used known disulphides whose corresponding reduced form are of low S-nucleophilicity depending upon resonance stabilization or thiol-thiontautomerism. Examples of such disulphides are 2,2'-dipyridyl disulphide, 4,4'-dipyridyl disulphide and corresponding compounds substituted in the pyridyl group, in which compounds the substituents are of such type and in such position as not to disturb the thiol-thion-tautomerism, for example 5-nitro-2-pyridyl disulphide and 5-carboxy-2-pyridyl-disulphide.

The reaction is carried out in aqueous solution at pH 2-9 and a temperature of 15°-30° C. with a large disulphide surplus.

There is preferably used, however, for both of these purposes a heterobifunctional agent of the formula

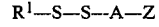

where $R^1$ is 2-pyridyl, 5-nitro-2-pyridyl or 4-pyridyl, A is a hydrocarbon residue having 1-10 carbon atoms, preferably 1-6 atoms, and Z is a group

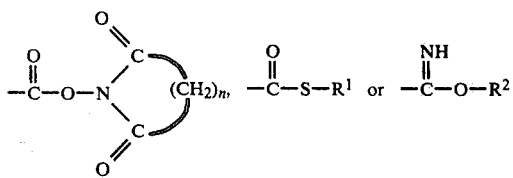 or acid addition salts of the last mentioned group, where n is 2 or 3, $R^1$ has the same significance as $R^1$ above and is equal thereto and $R^2$ is methyl or ethyl.

Compounds of the formula I can be prepared in a number of different ways. (See also patent application Ser. No. 882,547 filed at the same time as this application). Those methods most preferred for preparing the compounds are the following:

Compounds of the formula I, in which Z is the group

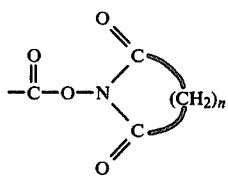

are prepared by reacting the disulphide of the formula $$R^1-S-S-A-COOH \qquad (II)$$

in which $R^1$ and A both have the above significance, with N-hydroxysuccinimide when n=2 ( or the analogous compound with n=3 when compounds with n=3 are desired) in the presence of a condensating agent.

The reaction is carried out in an organic solvent at a temperature of 10°-30° C. A suitable solvent is, for example, methylene chloride, ethyl acetate and dioxane. The reaction time varies with the selection of reaction components and reaction temperature.

The condensating agent used may be one which is common in esterifying reactions, such as N,N'-dicyclohexylcarbodiimide.

The starting compound of formula Ii can be prepared by reacting a mercaptoalkyl carboxylic acid of the formula $$HS-A-COOH \qquad (III)$$

with a dipyridyl disulphide of the formula $$R^1-S-S-R^1 \qquad (IV)$$

in which formulae A and $R^1$ both have the above significance.

This reaction is carried out in an organic solvent at a temperature of 10°-30° C. A suitable solvent in this respect is, for example, ethanol, ethyl acetate and dioxane. The reaction time varies with the choice of reaction components and reaction temperature.

Compounds of the formula I, in which Z is the group

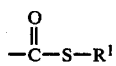

are prepared by reacting a disulphide of the formula II with a corresponding thiopyridone in the presence of a condensating agent in an organic solvent at initially low temperature, e.g. −20° C., for approximately 1-2 h, and thereafter at ambient temperature (e.g. +20° C.). The solvent may conveniently be, for example, methylene chloride, ethyl acetate and dioxane. The condensating agent used is preferably N,N'-dicyclohexylcarbodiimide.

The starting material used is, advantageously, a mixture obtained by reacting a compound of the formula III with a compound of the formula IV Compounds of the formula I, in which Z is the group

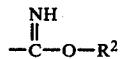

are prepared by reacting a thiolimidate of the formula

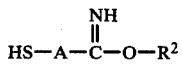

where $R^2$ and A have the above significance, with a pyridyl disulphide of the formula $R^1-S-S-R^1$, where $R^1$ has the above significance, in an organic solvent. The solvent used may, for example, be methanol containing approximately 10% glacial acetic acid.

The use of these agents can be illustrated by the following list of reactions, in which the bifunctional agent is, by way of example, N-succinimidyl-3(2-pyridyldithio)-propionate:

A.

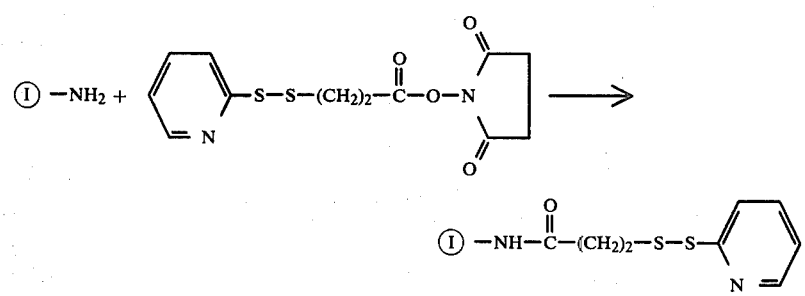

-continued

B. 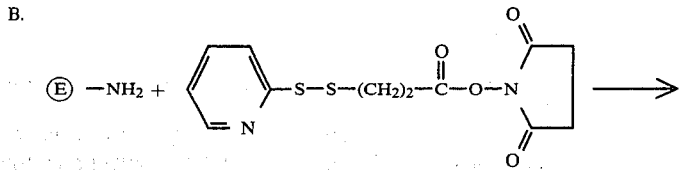

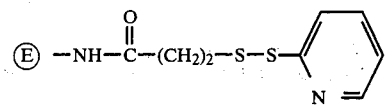

C. 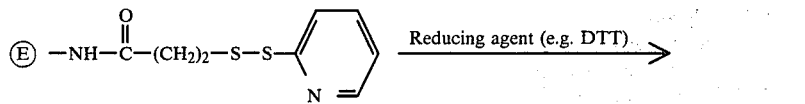

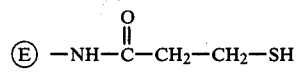

D. 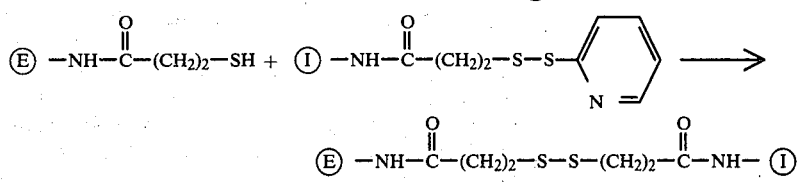

In the formulae given above (I)—NH₂ is an immunoglobulin molecule and (E)—NH₂ is an example of an indicatable group, e.g. an enzyme or a group containing one or more radioactive atoms. In the reduction illustrated in step C above there can be used, for example, DTT (dithiothreitol). With this reducing agent it is possible, for example, to reduce protein-bound pyridyl disulphide structures without at the same time reducing native disulphide bridges in the protein. This is achieved by effecting the reduction process at pH 3–5 with surplus DTT or at a higher pH with a lower surplus of DTT or an equimolar amount thereof.

The degree of substitution of thiol and disulphide can be readily influenced in this conjugating method, by varying the molar surplus of reactant or by varying the pH in the range 5–8. For example, there can be prepared bimolecular conjugates containing, e.g., an enzyme molecule (as the indicatable group) and an immunoglobulin-molecule (e.g. an antibody) by introducing 1 thiol group and 1 disulphide structure in respective molecules and permitting the modified molecules to react by means of thiol disulphide exchange. Since the thiol disulphide exchange reaction requires a reactive thiol and a disulphide structure and only one of these groups is present in each type of molecule, a conjugate comprising only one type of molecule can be avoided. Trimolecular or polymolecular conjugates can be obtained in a similar manner. Similarly, other indicatable groups can, of course, be bound to said immunoglobulin via splittable —S—S—bridges between the indicatable group and said immunoglobulin.

The aforementioned thiol disulphide exchange reactions can be carried out in an aqueous environment at pH 2–8 and a temperature of 15°–30° C.

In certain instances it may be desirable to avoid a direct conjugation of the analytically indicatable group to the immunoglobulin component. For example, the two types of molecules may unfavourably influence each others activity by e.g. hydrophobic interaction and/or effects of charges. In such cases, it may be suitable to use an inert, soluble carrier for both the analytically indicatable group and the immunoglobulin component, which are then each coupled to said soluble carrier with bridges of the aforementioned type comprising or containing the group —S—S—, whereby they are separated from each other. The sensitivity of a test based on such conjugates can be increased by attaching a large number of analytically indicatable groups to a soluble carrier, to which there is simultaneously coupled only one or a few immunoglobulin molecules.

The water-soluble carrier mentioned in the aforegoing may be, for example, dextran, a dextran derivative, biopolymers, and other polymers which are inert in the system and which are soluble in the liquid in whose presence the immunochemical reaction is carried out.

The coupling is carried out, for example, by introducing disulphide structures into the carrier and SH-groups into the label and the immunoglobulin component which are then coupled to the polymer by thiol disulphide exchange reaction. There can be used for the purpose of coupling either the immunoglobulin component or the label to the soluble carrier other methods which are known for coupling such substances to a carrier, since it is not necessary to be able to split both of the substances from said carrier.

When a particularly high sensitivity in the analysis is wanted the agent consists in accordance with a particularly valuable embodiment of the invention in labelled immunoglobulin consisting of a multiconjugate of a plurality of analytically indicatable groups linked together between themselves by splittable —S—S— bridges, said multiconjugate of indicatable groups in its turn also being bound to said immunoglobulin with a splittable —S—S— bridge.

The invention will now be described in more detail in the following with reference to a number of examples.

EXAMPLE 1

Sheep-antirabbit IgG-antibody-α-amylase conjugate (a) Thiolated α-amylase 6 mg of α-amylase ("bacterial type IIA" 4×cryst. from Sigma, USA) were dissolved in 2 ml of 0.1 M NaHCO$_3$. The solution was percolated with oxygen-free nitrogen gas and placed under a nitrogen gas atmosphere. 3 mg of methyl-4-mercaptobutyrimidate hydrochloride were added and the reaction mixture vigorously shaken. The reaction was permitted to continue for 30 minutes in the nitrogen gas atmosphere, whereafter surplus imidate and other low molecular weight components were removed from the thiolated α-amylase by gel filtration on Sephadex ® G-25 (beads of dextran cross-linked with epichlorohydrin from Pharmacia Fine Chemicals AB, Uppsala, Sweden) (the medium used was 0.1 M NaH$_2$PO$_4$). The thiolated α-amylases were found to contain 1.4 mole SH/mole protein.

(b) α-amylase containing pyridyl disulphide groups

The α-amylase thiolated in accordance with (a) above (in approx. 3 ml of 0.1 M NaH$_2$PO$_4$) was admixed with 1 ml of 8 mM bis-5(carboxy-2-pyridyl)-disulphide (aqueous solution pH ~6.5). After reacting for 2 h at +23° C., the reaction mixture was dialyzed against 0.1 M NaH$_2$PO$_4$ (3×2000 ml, 3 h in each bath), whereafter surplus reactant together with other low-molecular weight components were removed from the modified α-amylase. The thiolated and disulphide-treated α-amylase was found to contain 1.0 mole carboxypyridyl disulphide groups/mole protein.

(c) Thilated sheep-antirabbitIgC-antibodies

In a manner corresponding to that described under (a) above, 10 mg of sheep-antirabbit-antibodies (prepared from sheep serum by Na$_2$SO$_4$ precipitation) were thiolated with 0.25 mg of methyl-4-mercaptobutyrimidate hydrochloride. The thiolated antibodies contained 1.2 mole SH/mole protein.

(d) Sheep-antirabbitIgG-antibody-α-amylase conjugate

The carboxypyridyl disulphide-α-amylase derivative produced in accordance with (b) above, in approx. 3 ml 0.1 M NaH$_2$PO$_4$, were mixed with the thiolated antibodies produced in accordance with (c) above, in approximately 3 ml. Subsequent to vigorously shaking the mixture, the reaction was allowed to take place at +23° C. The reaction could be followed spectrophotometrically at 343 nm, since carboxy-2-thiopyridone, which is released during the thiol disulphide exchange reaction, has an extinction maximum at this wavelength. The reaction was interrupted after 10 h.

The reaction mixture was gel-filtered on Sepharose ® 6B (beads of agarose from Pharmacia Fine Chemicals AB, Uppsala, Sweden) and the different fractions analysed, whereupon it was found that 40% of the α-amylase activity supplied to the reaction mixture had been conjugated to antibodies. The conjugate formed, which judging from the gel filtration was bimolecular (small quantities of tri- and termolecular material were also found), was also found to be immunologically active. The gel-filtered conjugate was stored in 0.3 M NaCl at +4° C.

EXAMPLE 2

Sheep-antirabbitIgC-antibody-α-amylase conjugate (a) Thiolated α-amylase 5 mg of α-amylase were dissolved in 0.5 ml of 0.1 M Na-phosphate buffer, pH 7.5, 75 μl N-succinimidyl-3(2-pyridyldithio)propionate (34 mM in 99.5% EtOH) were added. Subsequent to vigorously shaking the mixture, the reaction was permitted to continue for 40 minutes at +23° C. The reaction mixture was gel filtered on Sephadex ® G-25 (beads of dextran cross-linked with epichlorohydrin from Pharmacia Fine Chemicals AB, Uppsala, Sweden) (the medium used was 0.3 M Na-phosphate buffer, pH 7.5). The thus obtained α-amylase-pyridyl disulphide derivative was then reduced by adding 50 μl of 50 mM dithiothreitol to the material obtained from the gel filtration (1.5 ml). The reduction was permitted to continue for 20 minutes at +23° C. Surplus dithiothreitol and other low-molecular weight components were removed by gel filtration on Sephadex ® G-25 (the medium used was 0.3 M NaCl). The thus thiolated α-amylase was found to contain 0.75 mole SH/mole protein.

(b) Sheep-antirabbitIgG-antibodies containing 2-pyridyl disulphide groups 1.2 mg of sheep-antirabbitIgG-antibodies (prepared from sheep hyperimmuno serum by immunosorbent purification) were dissolved in 0.5 ml of 0.1 M Na-phosphate buffer, pH 7.5. 15 μl of N-succinimidyl-3(2-pyridyldithio)propionate (5.9 mM in EtOH) were added. After shaking the reaction mixture vigorously, the reaction was permitted to take place for 40 minutes at +23° C. Surplus reagent and other undesirable low molecular weight components were removed by gel filtration on Sephadex ® G-25 (the medium used was 0.3 M NaCl).

The thus modified sheep-antirabbitIgG-antibodies were found to contain 2 mole 2-pyridyl disulphide groups/mole protein.

N-succinimidyl-3(2-pyridyldithio)propionate can be prepared in the following manner:

1.9 g (8.6 mmole) of 2,2'-dipyridyl disulphide is dissolved in 10 ml of ethyl acetate. A solution of 0.9 g (8.6 mmole) of 3-mercaptopropionic acid in 10 ml ethyl acetate is added dropwise for 15 minutes whilst stirring, at the same time as 0.5 mg (2 drops) of boron trifluoride etherate is added to the reaction mixture. After 20 h at room temperature and under agitation, the reaction mixture is vaporized (Büchi Rotavapor, <40° C.) and the solid yellow residue is slurried in 10 ml (cold) (+4° C.) ethyl acetate and filtered. 0.68 g (5 mmole) of N-hydroxysuccinimide is then added to the filtrate, whereafter 1.03 g (5 mmole) of dicyclohexylcarbodiimide dissolved in 10 ml dry ethyl acetate is added dropwise for 15 minutes whilst stirring at room temperature. The reaction is permitted to continue whilst stirring for 5 h at room temperature, whereafter the reaction mixture is cooled to +4° C. and the precipitated dicyclohexylcarbamide filtered off. The slightly yellow solution is vaporized and the oil dissolved in ethanol and permitted to crystallize at −20° C. Yield 45%. Melting point 78.5°–80.5° C.

(c) Sheep-antirabbitIgG-antibody-α-amylase conjugate 1.2 mg of sheep-antirabbitIgG-antibody-2-pyridyl disulphide (8 nmole protein containing 17 nmole of 2-pyridyl disulphide groups) (from (b) above) in 1 ml of 0.3 M NaCl were mixed with 5 mg of thiolated α-amylase (100 nmole containing 75 nmole SH-groups) (from (a) above) in 2 ml of 0.3 M NaCl. 0.1 ml of 0.1 M Na-phosphate buffer, pH 7.5, wax added and the reaction permitted to take place for 18 h at +4° C.

Gel filtration of the reaction mixture on Sephadex$^{(R)}$ G-200 (beads of dextran cross-linked with epichlorohydrin from Pharmacia Fine Chemicals AB, Uppsala, Sweden) and analysis of the fractions showed that 80% of the antibodies added had conjugated. The formed conjugate was mainly bimolecular (small quantities of tri- and termolecular material could also be observed). The conjugate was found to be both enzymatically and immunologically active and could be used for quantitative determination of rabbitIgG in the conventional sandwich-technique. Fractions containing conjugate were combined and concentrated to 290 μg (conjugated antibodies)/ml and stored in 0.3 M NaCl at +4° C.

EXAMPLE 3

Sheep-antirabbitIgG-antibody-(alkaline-phosphatase)-conjugate (a) Alkaline phosphatase containing 2-pyridyl disulphide groups 4 mg of alkaline phosphatase (from calf intestine, Boehringer Mannheim AG, West Germany) were dissolved in 2 ml of 0.1 m Na-phosphate buffer, pH 7.5. 150 μl of N-succinimidyl-3(2-pyridyldithio)propionate (1.7 mM in 99.5% ethanol) were added. Subsequent to vigorously shaking the reaction mixture, the reaction was permitted to continue for 40 minutes at +23° C. The reaction mixture was then gel filtered on Sephadex$^{(R)}$ G-25 (the medium used was the same phosphate buffer as above).

The thus modified alkaline phosphatase contained 1 mole pyridyl disulphide groups/mole protein.

(b) Thiolated sheep-antirabbitIgG-antibodies 2.5 mg sheep-antirabbitIgG-antibodies (prepared from sheep-serum by Na$_2$SO$_4$-precipitation) were dissolved in 0.5 ml of 0.1 M Na-phosphate buffer, pH 7.5. 40 μl of N-succinimidyl-3(2-pyridyldithio)propionate (1.7 mM in 99.5% ethanol) were added. After shaking the mixture vigorously, the reaction was permitted to continue for 40 minutes at +23° C. Surplus reactant and other undesirable low molecular weight components were removed by gel filtration on Sephadex$^{(R)}$ G-25 (the medium used was 0.1 M Na-acetate buffer pH 5). The thus obtained sheep-antirabbitIgG-antibody-pyridyl disulphide derivative was then reduced by adding 50 μl of 50 mM dithiothreitol to the void material from the gel filtration (approx. 1.5 ml). The reduction was continued for 30 minutes at +23° C. Surplus dithiothreitol and other low molecular weight components were removed by gel filtration on Sephadex$^{(R)}$ G-25 (the medium used was 0.3 M NaCl). The thus thiolated sheep antirabbitIgG-antibodies contained 2 mole SH/mole protein.

(c) Sheep-antirabbitIgG-antibody-(alkaline phosphatase)-conjugate

The thiolated sheep-antirabbitIgG-antibodies (approx. 2.5 mg) according to (b) in 1 ml of 0.3 M NaCl were mixed with alkaline phosphatase-2-pyridyl disulphide derivative (approx. 4 mg), prepared in accordance with (a) above, in 3.5 ml of 0.1 M Na-phosphate buffer, pH 7.5. The reaction mixture was shaken and the reaction permitted to continue for 24 h at +23° C. Gel filtration of the reaction mixture on Sephadex$^{(R)}$ G-200 (the medium used was 0.3 M NaCl) and analysis of the fractions showed that a "low molecular conjugate" (bi- and trimolecular) had been formed. The fractions containing conjugate were combined and concentrated to approx. 100 μg (with respect to antibodies)/ml. The conjugate was enzymatically and immunochemically active and could be used for quantitative determination of rabbitIgG.

EXAMPLE 4

Sheep-antirabbitIgG-antibody-(alkaline phosphatase)-conjugate (a) Alkaline phosphatase containing 2-pyridyl disulphide groups 4 mg of alkaline phosphatase (as in example 3) were dissolved in 2.5 ml of 0.1 M Na-phosphate buffer, pH 7.5. 100 μl of N-succinimidyl-3-(2-pyridyldithio)propionate (5.9 mM in 99.5% ethanol) were added. After shaking the reaction mixture, the reaction mixture was left to stand for 45 minutes at +23° C. Surplus reactant and other undesirable low-molecular weight components were removed by gel filtration on Sephadex$^{(R)}$ G-25 (the medium used was 0.1 M Na-phosphate buffer, pH 7.5). The obtained alkaline phosphatase derivative contained 1.1 mole of 2-pyridyl disulphide groups/mole of protein.

(b) Thiolated sheep-antirabbitIgG-antibodies

Immunosorbent purified sheep-antirabbitIgG-antibodies were thiolated in the manner described in Example 3.

(c) Sheep-antirabbitIgG-antibody-(alkaline phosphatase)-conjugate

The thiolated sheep-antirabbitIgG-antibodies (approx. 1.2 mg) from (b) in 1 ml of 0.3 M NaCl was mixed with (alkaline phosphatase)-2-pyridyl disulphide derivative (approx. 4 mg) from (a) in 3.5 ml of 0.1 M Na-phosphate buffer, pH 7.5. The reaction mixture was shaken and the reaction was continued at +23° C. for 24 h.

Gel filtration of the reaction mixture on Sephadex$^{(R)}$ G-200 (medium used was 0.3 M NaCl) showed that a bi-molecular conjugate had been formed and also, to some extent, a tri-molecular conjugate. The conjugate was both enzymatically and immunologically active and could be used for quantitative determination of rabbitIgG. The conjugate was stored in 0.3 M NaCl at +4° C.

EXAMPLE 5

Sheep-antirabbitIgG-antibody-catalase conjugate (a) Catalase containing 2-pyridyl disulphide groups 5 mg of catalase (from beef liver from Koch-Light Labs., Ltd., England) were dissolved in 1 ml of 0.1 M Na-phosphate buffer, pH 7.5. 50 μl of N-succinimidyl-3-(2-pyridyldithio)propionate (1.7 mM in 99.5% ethanol) were added. Subsequent to shaking the reaction mixture, the reaction was permitted to continue for 45 minutes at +23° C. The reaction mixture was then gel filtered on Sephadex$^{(R)}$ G-25 (the medium used was 0.1 M Na-phosphate buffer, pH 7.5).

The modified catalase contained 0.7 mole of 2-pyridyl disulphide groups/mole of enzyme.

(b) Thiolated sheep-antirabbitIgG-antibodies 1.1 mg of sheep-antirabbitIgG-antibodies (the same type as that in Example 1) were dissolved in 0.5 ml of 0.1 M Na-phosphate buffer, pH 7.5. 20 μl of N-succinimidyl-3(2-pyridyldithio)propionate (1.7 mM in 99.5% ethanol) were added. After shaking the reaction mixture, the reaction was permitted to continue for 45 minutes at +23° C. Surplus reactant and other undesirable low molecular weight components were removed by gel filtration on Sephadex$^{(R)}$ G-25 (the medium used was 0.1 M Na-acetate buffer, pH 5).

0.1 ml of 50 mM dithiothreitol was added to the void material (1.55 ml). The reduction was permitted to continue for 30 minutes at +23° C. Surplus dithiothreitol was then removed by gel filtration on Sephadex$^{(R)}$ G-25 (the medium used was 0.3 M NaCl). Analysis of the fractions showed that a catalase-sheep-antirabbit-IgG-antibody-conjugate had been formed.

The formed conjugate, which judging from the gel filtration had a molecular weight of 400 000-700 000, was found to be both enzymatically an immunochemically active and could be used for the quantitative determination of rabbitIgG with the aid of the usual sandwich technique. The gel filtered conjugate was stored in 0.3 M NaCl at +4° C.

EXAMPLE 6

Sheep-antirabbitIgG-antibody-dextran-α-amylase conjugate (a) 2-pyridyl disulphide derivative of dextran 1 g of bromohydroxypropyldextran was dissolved in 12.5 ml of distilled water and 3.8 g of $Na_2S_2O_3 \times 7 H_2O$ were added. The reaction was permitted to take place at 100° C. for 3 h. The mixture was then dialyzed against $H_2O$ (2×2 l for 24 h and 1×10 l for 6 h).

The content of the dialysis bag was freeze-dried and is referred to hereinafter as Bunte salt dextran. Analysis showed that the dextran derivative contained 1.2 mmole S/g dry derivative. 1 g of Bunte salt dextran was dissolved in 10 ml of 50% ethanol-50% 0.1 M Na-phosphate buffer, pH 8.3. 0.7 g of 2,2'-dipyridyl disulphide was added and the mixture heated to 60° C. and maintained at this temperature for 24h. The reaction mixture was then dialyzed against 50% ethanol 3×3 l (each dialysis for 6 h) and against distilled water 3×3 l (each dialysis for 2 h). Analysis showed that the 2-pyridyl disulphide dextran contained 430 μmole of 2-pyridyl disulphide groups/g derivative.

(b) Thiolated sheep-antirabbitIgG-antibodies 2.6 mg of sheep-antirabbitIgG-antibodies (the same type as that in Example 1) were dissolved in 1 ml of 0.1 M Na-phosphate buffer, pH 7.5. 120 μl of N-succinimidyl-3(2-pyridyldithio)propionate (1.6 mM in 99.5% ethanol) were added and the reaction was permitted to continue (subsequent to shaking the mixture) at +23° C. for 30 minutes. The reaction mixture was then gel filtered on Sephadex$^{(R)}$ G-25 (the medium used was 0.1 M Na-acetate buffer, pH 5.0). The void material (2.5 ml) (2-pyridyl disulphide-sheep-antirabbitIgG-antibody-derivative) was reduced with 64 μl of 50 mM dithiothreitol. After 15 minutes at +23° C., surplus dithiothreitol was removed by gel filtration on Sephadex$^{(R)}$ G-25 (the medium used was 0.3 M NaCl). A void volume of 3.5 ml was obtained.

(c) Thiolated α-amylase

This was prepared in the manner described in Example 1 (a).

(d) Sheep-antirabbitIgG-antibody-dextran-α-amylase conjugate 2.4 mg of thiolated α-amylase from (c) above (in 1.5 ml) and 2.6 mg of thiolated sheep-antirabbitIgG-antibodies from (b) above in 3.5 ml were mixed with 1.6 mg of 2-pyridyl disulphide dextran in 1 ml of 0.1 M Na-phosphate buffer, pH 7.5. Subsequent to shaking the mixture, the mixture was allowed to stand for 10 minutes and then gel filtered on Sepharose$^{(R)}$ 6B (beads of agarose from Pharmacia Fine Chemicals AB, Uppsala, Sweden) with 0.3 M NaCl as the medium.

Analysis of the different fractions showed that 80% of the α-amylase activity had conjugated. A conjugated immunological activity could also be observed. The fractions containing conjugate were combined and stored at +4° C. When the conjugate was used in the usual sandwich-technique for the determination of rabbitIgG an amplification effect was observed due to the plurality of enzyme label groups in the conjugate.

EXAMPLE 7

Rabbit-antihumanFcγ-antibody-peroxidase conjugate (a) Peroxidase containing 2-pyridyl disulphide groups 10 mg of peroxidase (from horse-radish, degree of purity 1 from Boehringer Mannheim AG, West Germany) in 2 ml of 0.1 M Na-phoosphate buffer, pH 7.5, were admixed with 0.35 ml of 14 mM N-succinimidyl-3(2-pyridyldithio)propionate. After 40 minutes reaction time, surplus reactant was removed by means of gel filtration on Sephadex$^{(R)}$ G-25 (the medium used as 0.1 M Na-phosphate buffer, pH 7.5). The thus obtained peroxidase-2-pyridyl disulphide derivative had a volume of 2.75 ml.

(b) Thiolated rabbit-antihumanFcγ-antibodies 4 mg of rabbit-antihumanFcγ-antibodies (prepared from rabbit serum by precipitation and immunosorbent purification) were dissolved in 1.5 ml of 0.1 M Na-phosphate buffer, pH 7.5. 60 μl of 1.3 mM N-succinimidyl-3(2-pyridyldithio)propionate in ethanol (99.5%) were added. The reaction mixture was shaken and then allowed to stand for 40 minutes at +23° C. Surplus reactants was removed by gel filtration on Sephadex$^{(R)}$ G-25 (the medium used was 0.1 M Na-acetate buffer, pH 4.8). The void fraction containing the modified antibodies were combined to a total of 2.5 ml. The reduction of the antibody derivative with dithiothreitol (see below) and determination of the amount of released 2-thiopyridone showed that the derivative contained approx. 2 mole 2-pyridyl disulphide groups/mole protein.

The antibody-2-pyridyl disulphide derivative (2.3 ml of the void material from above) was reduced with 0.1 ml of 50 mM dithiothreitol at +23° C. for 30 minutes. Surplus dithiothreitol was then removed by means of gel filtration on Sephadex$^{(R)}$ G-25 (the medium used was 0.3 M NaCl). The thiolated antibodies were obtained in a volume of approx. 3.5 ml (the void).

(c) Rabbit-antihumanFcγ-antibody-peroxidase conjugate

Peroxidase-2-pyridyl disulphide derivative from (a) in 2.75 ml of 0.1 M Na-phosphate-buffer, pH 7.5, was mixed with the thiolated antibodies from (b) in 3.5 ml of 0.1 M Na-phosphate buffer, pH 7.5. Subsequent to being shaken, the mixture was allowed to stand at +4° C. for 24 h. 2.0 ml of the reaction mixture was then gel filtered on Sephadex$^{(R)}$ G-25 (the medium used was 0.3 M NaCl) and the remainder (6.25-2=4.25 ml) on Sephadex$^{(R)}$ G-200 (the medium used was 0.3 M NaCl). The conjugate, which was obtained as void material upon gel filtration on Sephadex$^{(R)}$ G-25, is designated conjugate solution I and the combined conjugate-containing fractions obtained when filtering on Sephadex$^{(R)}$ G-200 are designated conjugate solution II.

Conjugate solution I contained approx. 250 μg conjugated antibodies/ml.

Conjugate solution II contained approx. 50 μg conjugated antibodies/ml.

The solutions wee stored at +4° C. The conjugates were enzymatically active and the antibodies in the conjugates were still immunochemically active and could combine with the corresponding antigen.

EXAMPLE 8

Sheep-antihumanIgG-antibody-α-amylase-multicomplex conjugate 30 mg of α-amylase (same type and pretreatment as in Example 1) were dissolved in 4.5 ml 0.1 M Na-phosphate-0.3 M NaCl pH 7.5. 100 μl 50 mM N-succinimidyl-3(2-pyridyldithio)propionate in abs. EtOH were added in portions of 25 μl at intervals of 5 minutes. After 40 minutes at +25° C. the reaction mixture was gel filtered on Sephadex$^{(R)}$ G-25 (medium used was 0.1 M Na-phosphate-0.3 M NaCl pH 7.5), surplus reactant and low molecular reaction products being removed. The void material containing modified α-amylase (2-pyridyl-disulphide-α-amylase) was pooled to 8 ml. The degree of substitution with respect to the content of 2-pyridyl disulphide was found to be 3.7 μmole 2-pyridyldisulphide groups/50 mg of α-amylase.

Another 2-pyridyl disulphide-α-amylase derivative was prepared as described above with the difference that 400 μl of 50 mM N-succinimidyl-3(2-pyridyldithio)propionate in abs. EtOH were added in portions of 100 μl at intervals of 5 minutes. The degree of substitution of this derivative was determined to be 7.5 μmole of 2-pyridyl disulphide groups/50 mg of α-amylase.

2.5 mg of 2-pyridyl disulphide-α-amylase containing 3.7 μmole 2-pyridyl disulphide groups/50 mg in 0.75 ml 0.1 M Na-phosphate-0.3 M NaCl pH 7.5 were mixed with 50 μl 50 mM dithiothreitol and reduced for 10 minutes at +25° C. Surplus dithiothreitol and low molecular weight reaction products were removed by gel filtration on Sephadex$^{(R)}$ G-25 (the medium used was 0.3 M NaCl).

The void, 2.5 ml, containing 2.3 mg of thiol-α-amylase, was mixed with 1.5 mg of 2-pyridyl-disulphide-α-amylase containing 7.5 μmole 2-pyridyl disulphide groups/50 mg in 0.75 ml 0.1 M Na-phosphate-0.3 M NaCl. After reaction for 60 minutes at 25° C. the reaction was cut off by the addition of 50 μl 20 mM 2,2'-dipyridyl disulphide in abs. EtOH. 1 drop of Tween-20 was added and the mixture was chromatographed on a column of Sepharose$^{(R)}$-6B (80 ml total volume) (the medium used was 0.3 M NaCl-0.5% Tween 20). The void material (about 15 ml) containing about 0.19 mg α-amylase aggregate/ml containing 2.4 μmole 2-pyridyl disulphide groups was pooled and stored at +4° C.

6 mg of sheep-antihuman IgG-antibodies (immunosorbent purified with γ-globulin-agarose sorbent prepared by coupling human electrophoretically purified γ-globulin to CNBr-activated Sepharose$^{(R)}$ 4B (Pharmacia Fine Chemicals AB, Uppsala, Sweden)) in 2.4 ml 0.1 M Na-phosphate-0.3 M NaCl pH 6.0 were mixed with 20 μl 50 mM N-succinimidyl-3(2-pyridyldithio)propionate in abs. EtOH. After 20 minutes at +25° C. surplus reactant was removed by gel filtration of the reaction mixture on Sephadex$^{(R)}$ G-25 (the medium used was 0.1 M Na-acetate-0.3 M NaCl, pH 5.0). The void, about 3.0 ml, containing about 5.5 mg 2-pyridyl disulphide antibodies was pooled and reacted with 0.2 ml 50 mM dithiothreitol in distilled H$_2$O. After reaction for 25 minutes surplus dithiothreitol was removed by gel filtration of the reaction mixture on Sephadex G-25 (the medium used was 0.3 M NaCl). The void, 5.0 ml, containing about 5 mg modified antibodies with a degree of substitution of about 2 μmole SH-groups per 160 mg of protein, was pooled.

About 0.2 mg of the antibodies thus thiolated in 0.2 ml of 0.3 M NaCl was mixed with 0.4 mg of the α-amylase aggregate (vide above) in 2.0 ml 0.1 M Na-phosphate-0.3 M NaCl-0.5% Tween 20. The reaction mixture containing sheep-antihuman IgG antibody-α-amylase multicomplex conjugate was stored at +4° C.

EXAMPLE 9

Sheep-antihumanIgG-antibody-glutathionefluorescein conjugate (a) Glutathione-fluorescein 100 mg of fluorescein isothiocyanate were reacted with 35 mg of oxidized glutathione in 4 ml of distilled H$_2$O. The reaction was carried out for 90 minutes at constant pH 9. The reaction mixture was gel filtered on a 100 ml column of Sephadex$^{(R)}$ G-25 (the medium used was 0.3 M NaCl). The fractions corresponding to the total volume were collected (10.3 ml with A 493=41.2). The pH-value was adjusted to 9 with a Na-borate buffer. The solution was then pumped through a column containing 2.2 ml of mercaptohydroxypropylagarose (prepared from agarose (Sepharose$^{(R)}$ 6B from Pharmacia Fine Chemicals AB, Uppsala, Sweden) according to Axen et al., Acta Chem. Scand. B 29 (1975) 471-474; gel containing 660 μmole SH/g dried gel was used) equilibrated with 0.1 M Na-borate buffer pH 9. The flow was 10 ml/h. The eluate was collected in 1 M Na-acetate pH 4 and the fluorescein and thiol contents thereof were determined. A fraction (3 ml) having a thiol concentration of 1.19 mM and a fluorescein concentration of 0.60 mM was used in the experiment below.

(b) Sheep-antihumanIgG-antibodies containing 2-pyridyl disulphide groups 5 mg of sheep-antihumanIgG-antibodies (immunosorbent purified with Sepharose$^{(R)}$-humanγ-globulin) were dissolved in 0.5 ml 0.1 M Na-phosphate buffer pH 7.5. 20 μl 10 mM N-succinimidyl-3-(2-pyridyldithio)propionate (in 99.5% ethanol) were added. After shaking the reaction mixture was allowed to stand at +23° C. for 40 minutes. Surplus reagent was then removed by gel filtration on Sephadex$^{(R)}$ G-25 (the medium used was 0.1 M Na-phosphate buffer pH 7.5).

(c) Sheep-antihumanIgG-antibody-glutathione-fluorescein conjugate 1.5 ml of the void material from (b) above (4.5 mg sheep-antihumanIgG-antibodies containing 2-pyridyl disulphide groups) were mixed with 3 ml of glutathione-fluorescein from (a) above. The mixture was allowed to stand at room temperature for 30 minutes and was then gel filtered on Sephadex$^{(R)}$ G-25 with 0.9% NaCl as the medium. Analysis showed that the void (6 ml) contained 3.2 mg sheep-antihumanIgG-antibodies with about 3.5 mole fluorescein/mole antibody.

The conjugate was stored dissolved in 0.9% by weight NaCl at +4° C.

Human IgG could in a sandwich procedure be detected with fluorescence technique by using this conjugate. In this connexion the radiation damping effect of the carrier polymer was eliminated by setting the glutathione-fluorescein free from the polymer reductively.

EXAMPLE 10

Sheep-antihumanIgG-antibody-glutathionedextranfluorescein conjugate (a) Glutathione-fluorescein About 3 ml derivative having a thiol concentration of about 1.2 mM and a fluorescein concentration of about 0.60 mM were prepared according to Example 9 (a).

(b) Sheep-antihumanIgG-antibody-dextran-glutathionefluorescein conjugate 5 g dextran T-70 (Pharmacia Fine Chemicals AB, Uppsala, Sweden) were dissolved in 20 ml 20% NaOH containing 1% $NaBH_4$. 5 g of 2-chloroethylamine hydrochloride were added and the mixture was stirred for 18 hours at +90° C. After cooling to +25° C. and neutralizing with 6 M HCl, the small amount of precipitate formed was removed by centrifugation. The supernatant was dialyzed against distilled water and freeze-dried.

5 g of aminoethyl dextran dry product was obtained. The nitrogen content was found to be 1.5%.

1 g of the aminoethyl dextran was dissolved in 30 ml 0.05 M Na-borate buffer pH 9 and N-succinimidyl-3(2-pyridyldithio)propionate (300 mg in 30 ml abs. ethanol) was added dropwise while stirring for 10 minutes. The reaction mixture was allowed to stand for additional 20 minutes whereafter 3 ml of concentrated acetic acid were added. The mixture thus obtained was dialyzed against 50% ethanol (3×2000 ml) for 48 h and then evaporated to 15 ml and freeze-dried.

1 g of dry product (2-pyridyl disulphide dextran) was obtained.

0.54 mg of thiolated sheep-antihumanIgG-antibodies containing about 2 μmole thiol groups/160 mg protein (prepared according to Example 8) in 0.3 M NaCl was mixed with 0.15 mg of 2-pyridyl disulphide dextran (vide above) dissolved in 0.1 ml Na-phosphate-0.3 M NaCl pH 7.5. The reaction mixture was carefully stirred for 48 h at +4° C. The pH-value was then adjusted to 5.0 by the addition of 2 M HCl. 30 μl glutathione-fluorescein solution (vide above) were then added. After 3 h at +25° C. the reaction mixture was applied to a Sephadex G-25 column (the medium used was 0.3 M NaCl) and the fractions corresponding to the void volume were pooled (about 2 ml).

The concentration of dextran was about 0.07 mg/ml, the fluorescein concentration about 5.5 μM and the sheep-antihumanIgG-antibody concentration about 0.24 mg/ml.

The conjugate thus obtained exhibited immunological activity and could be used for the quantitative determination of human gammaglobulin in a sandwich procedure, whereby the glutathionefluorescein after binding of the antibody-dextran-glutathionefluorescein conjugate to the insoluble carrier polymer was liberated by reduction and thus could be measured fluorometrically in the outer solution without any disturbing influence from solid carrier material and conjugate neighbours.

EXAMPLE OF APPLICATION

Quantitative determination of human γ-globulin using sheep-antihumanIgG-antibody-α-amylase multicomplex conjugate About 50 μg (dried derivative) of agarose-sheep-antihumanIgG-antibody derivative (prepared by coupling immunosorbent purified sheep-antihumanIgG-antibodies to CNBr-activated Sepharose$^{(R)}$ 4B) containing about 400 ng antibodies and suspended in 300 μl 0.3 M NaCl-0.5% Tween 20 are added to each tube in a series of polystyrene tubes (3 ml) containing varying amounts (1–500 ng) of human γ-globulin dissolved in 100 μl 0.1 M Na-phosphate-0.3 M NaCl-0.5% Tween 20 pH 7.4. A number of tubes containing only buffer and a number of tubes containing aminoethyl-agarose (prepared by coupling ethanolamine to CNBr-activated Sepharose$^{(R)}$ 4B) were used as blanks.

The tubes were incubated for about 18 hours at +25° C. while being shaken carefully. The agarose gel in each tube was then washed by a repeated centrifuging-decanting procedure with 6×2 ml 0.3 M NaCl-0.5% Tween.

After the last washing, the supernatant was sucked off to 0.3 ml and 100 μl of the reaction mixture from Example 8 above containing sheep-antihumanIgG-antibody-α-amylase-multicomplex conjugate (about 400 ng with respect to antibodies) were added to each tube which then was incubated during careful shaking for 4 hours at +25° C. The solid material of each tube was washed again as described above with 6×2 ml 0.3 M NaCl-0.5% Tween 20.

1.0 ml 10 mM dithiothreitol in 0.1 M Na-phosphate-0.3 M NaCl pH 8 was added to the tubes (0.3 ml suspension). After reduction for 60 minutes (during which the α-amylase-multicomplex was set free from the immobilized immunocomplex and was split into smaller units) 1.0 ml of a suspension of Phadebas$^{(R)}$ amylase test (1 tablet/4 ml, Pharmacia Diagnostics AB, Uppsala, Sweden) was added and the tubes were incubated again for 60 minutes at +25° C. whereafter the reaction was cut off by the addition of 0.5 ml 0.5 M NaOH. After removing undissolved starch polymer by filtration, the extinction of the blue-coloured filtrate was determined at 620 nm. The extinction values are related to the α-amylase activity set free which is related to the amount of bound conjugate which in turn is related to the amount of bound γ-globulin and thus is a measure of the γ-globulin concentrations of the test solutions. Human γ-globulin could be detected down to a concentration of <1 ng/ml in this way.

What is claimed is:

1. A reagent for use in immunochemical assay methods carried out in the presence of an aqueous liquid, wherein said reagent comprises a conjugate of one or more molecules of immunoglobulin and one or more units of an analytically indicatable group, which molecules and units are bound together via bridges containing the group —S—S—, said conjugate being soluble in said aqueous liquid.

2. A reagent according to claim 1, characterized in that the analytically indicatable group is an enzymatically active, radioactive or fluorescent group.

3. A reagent according to claim 1, characterized in that said immunoglobulin is an antibody directed against an antigen or hapten.

4. A reagent according to claims 1, 2 or 3 characterized in that the molecules of immunoglobulin and the units of the analytically indicatable group are each bound to a water-soluble carrier, at least one of said immunoglobulin and said group being bound to the carrier via bridges containing the group —S—S—.

5. A reagent according to claim 2, characterized in that said immunoglobulin is an antibody directed against an antigen or hapten.

* * * * *